United States Patent
Lindahl

(10) Patent No.: US 9,561,279 B2
(45) Date of Patent: *Feb. 7, 2017

(54) ANTIFUNGAL COMPOSITION

(71) Applicant: Moberg Pharma AB, Bromma (SE)

(72) Inventor: Ake Lindahl, Malmo (SE)

(73) Assignee: Moberg Pharma AB, Bromma (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/534,640

(22) Filed: Nov. 6, 2014

(65) Prior Publication Data

US 2015/0250878 A1 Sep. 10, 2015

Related U.S. Application Data

(63) Continuation of application No. 13/984,657, filed as application No. PCT/EP2012/052327 on Feb. 10, 2012, now Pat. No. 8,952,070.

(30) Foreign Application Priority Data

Feb. 11, 2011 (SE) ...................... 1150107

(51) Int. Cl.
- A01N 33/24 (2006.01)
- A61K 31/13 (2006.01)
- A61K 31/135 (2006.01)
- A61K 47/14 (2006.01)
- A61K 9/00 (2006.01)
- A61K 31/00 (2006.01)
- A61K 31/137 (2006.01)
- A61K 47/10 (2006.01)
- A61K 47/12 (2006.01)
- A61K 47/18 (2006.01)
- A61K 9/08 (2006.01)

(52) U.S. Cl.
CPC ............. *A61K 47/14* (2013.01); *A61K 9/0014* (2013.01); *A61K 9/08* (2013.01); *A61K 31/00* (2013.01); *A61K 31/13* (2013.01); *A61K 31/137* (2013.01); *A61K 47/10* (2013.01); *A61K 47/12* (2013.01); *A61K 47/183* (2013.01)

(58) Field of Classification Search
CPC ...... A61K 31/137; A61K 31/00; A61K 31/13; A61K 47/10; A61K 47/12; A61K 47/183; A61K 9/0014

See application file for complete search history.

(56) References Cited

U.S. PATENT DOCUMENTS

| | | | |
|---|---|---|---|
| 5,525,635 A | 6/1996 | Moberg | |
| 6,509,319 B1 | 1/2003 | Raad et al. | |
| 7,074,392 B1 | 7/2006 | Friedman et al. | |
| 7,678,366 B2 | 3/2010 | Friedman et al. | |
| 7,820,720 B2 | 10/2010 | Cevc et al. | |
| 8,952,070 B2 | 2/2015 | Lindahl | |
| 2004/0096410 A1 | 5/2004 | Maley et al. | |
| 2006/0078599 A1 | 4/2006 | Ebmeier et al. | |
| 2007/0243222 A1 | 10/2007 | Lawyer et al. | |
| 2008/0038219 A1 | 2/2008 | Mosbaugh et al. | |
| 2008/0188568 A1 | 8/2008 | Suvanprakorn et al. | |
| 2010/0158961 A1 | 6/2010 | Gunn et al. | |
| 2012/0309843 A1 | 12/2012 | Buyuktimkin et al. | |

FOREIGN PATENT DOCUMENTS

| | | | |
|---|---|---|---|
| CN | 1939539 A | 4/2007 | |
| DE | 19921794 A1 | 11/2000 | |
| JP | 2006182733 A | 7/2006 | |
| WO | WO 9937172 A1 * | 7/1999 | ............... A23B 4/10 |
| WO | WO-2004/021968 A2 | 3/2004 | |
| WO | WO-2006/042324 A2 | 4/2006 | |
| WO | WO-2006/103638 A2 | 10/2006 | |
| WO | WO-2007/076619 A1 | 7/2007 | |
| WO | WO-2007/094999 A2 | 8/2007 | |
| WO | WO-2008/097530 A1 | 8/2008 | |
| WO | WO-2008/121709 A1 | 10/2008 | |
| WO | WO-2009/140215 A2 | 11/2009 | |
| WO | WO-2011/019317 A1 | 2/2011 | |
| WO | WO-2011/079234 A2 | 6/2011 | |
| WO | WO-2012/017371 A1 | 2/2012 | |

OTHER PUBLICATIONS

Xiaojian Wang, et al., "Evaluation of Therapeutic Effect of Terbinafine Nail Lacquer for Onychomycosis," Acta Academiae Medicinae Qingdao Universitatis, 2006, vol. 42, No. 3 [Abstract only].

Final Report on the Safety Assessment of EDTA, *Int. J. Toxicology*, 2002, 21:95-142.

Mertin et al., "In-vitro Permeability of the Human Nail and of a Keratin Membrane from Bovine Hooves: Prediction of the Penetration Rate of Antimycotics through the Nail Plate and their Efficacy", *J. Pharm. Pharmacol.*, 1997, 49:866-872.

Pharmaceutical Preformulation and Formulation, Eds. Gibson, 2001, CRC Press, pp. 206-207.

Report on the Safety Assessment of EDTA, *Int. J. Toxicology*, 2002, 21:95-142.

Declaration of Dr. Peter Kaufmann, dated Mar. 11, 2014, submitted in U.S. Appl. No. 13/984,657, filed: Aug. 9, 2013, Title: Novel Antifungal Composition.

* cited by examiner

*Primary Examiner* — Jean Cornet

(74) *Attorney, Agent, or Firm* — McCarter & English, LLP; Steven G. Davis

(57) ABSTRACT

There is provided a pharmaceutical composition for the treatment of fungal infection of the nail comprising a antifungal allylamine compound present in an amount of about 10%, an organic acid or an ester thereof, a diol and a sequestering agent where the pharmacological composition is essentially water-free.

10 Claims, No Drawings

ANTIFUNGAL COMPOSITION

TECHNICAL FIELD

This invention comprises compositions for the treatment of fungal infection of the nail. The composition is intended for the local treatment of nails and enables the penetration of antifungal substances into and through the nail.

BACKGROUND ART

The problem of fungal infections of the nail (onychomycosis) followed by the destruction of the nail has been subject to numerous efforts but so far no clinically satisfactory solution is at hand. However, there is a general agreement that if a sufficient amount of a potent antifungal compound can be distributed throughout the nail and in the nail bed, the infection will be cured and the destruction of the nail will end.

PRIOR ART

In prior art several attempts to increase penetration of an antifungal agent has been described.

U.S. Pat. No. 7,820,720 describes a pharmaceutical formulation suitable for topical delivery of terbinafine, comprising, in an aqueous solution, i) terbinafine or a pharmaceutically acceptable salt thereof in an amount ranging from about 0.5% to about 10% by weight, ii) a phospholipid in an amount ranging from about 4% to about 7% by weight, and iii) a non-ionic surfactant in an amount ranging from about 1% to about 4%.

U.S. Pat. No. 7,678,366 describes a sustained release therapeutic nail varnish for treating a fungal infection, of the nail and/or surrounding tissue, comprising: a. an antifungal amount of naftifine or terbinafine; b. a keratolytic agent; c. at least about 3% of a humectant wherein the humectant is sorbitol, glycerol, or a mixture thereof; d. water in an amount of 0.5 to less than about 5% of the varnish solution; e. a hydrophobic methacrylic polymer in an amount of about 8% to about 35% based on the total weight of the non-volatile components; and f. a volatile solvent selected from the group consisting of an alcohol, a ketone, and mixtures thereof in an amount of about 60% to about 90%, relative to the total weight of the composition.

U.S. Pat. No. 7,074,392 discloses a sustained release therapeutic nail varnish composition comprising: (a) an antifungal effective amount of an antifungal agent; (b) a keratolytic agent in an amount sufficient to increase and facilitate penetration of the antifungal agent into the nail; (c) more than 3% (w/w) of a humectants, (d) water in an amount sufficient to hydrate the nail; (e) a liquid nail lacquer component comprising a polymeric film forming agent and a volatile solvent, said agent selected to form a sustained release film upon application of said composition on a nail and evaporation of said volatile solvent.

SUMMARY OF THE INVENTION

It is desirable to have antifungal compositions for the treatment of onychomycosis with high penetration.

Furthermore, it is desirable to have a formulation with a high concentration of an active antifungal compound.

Moreover, it is often desirable to have the antifungal compound dissolved in the formulation, that is, it is not precipitated.

An object of the present invention is to address at least some of the issues outlined above. It is therefore provided, in a first main aspect of the invention, a pharmaceutical composition for the treatment of fungal infection of the nail comprising an antifungal allylamine compound present in an amount of more than 5%, an organic acid or an ester thereof, a diol and a sequestering agent wherein said pharmaceutical composition is essentially water-free.

DETAILED DESCRIPTION

In the following, a detailed description of the invention will follow.

As used herein, unless stated otherwise, the amounts of components in percent refer to percent by weight and are based on the total weight of the composition.

The term "about" is used to denote a deviation of +/−10% of the stated value, where applicable. For example, "about 20%" denotes a value of from 18% to 22%.

The composition is essentially water free. No water has been added to the formulation. However, there can nevertheless still be trace amounts of water in the composition since certain of the components may contain small amounts of water. The trace amounts of water are less than 5%, more preferably less than 3%, more preferably 2%, more preferably less than 1%, more preferably less than 0.5% and most preferably less than 0.3%.

If water is added to the formulation, the antifungal compound will precipitate and hence become inactivated, which is undesirable in this system because a limited amount of terbinafine will be therapeutically available after application.

An additional advantage of the invention that it contains a high concentration, more than 5%, of the antifungal substance. This increases the efficacy of the antifungal composition.

The antifungal allylamine is dissolved in the composition, Thus, the formulation is present as a solution, that is, a one phase system.

Allylamine antifungal agents, in particular terbinafine and naftifine, are preferred antifungal agents of the present invention. These inhibit the growth of fungi by blocking the enzyme squalene epoxidase, a key enzyme in fungal ergosterol biosynthesis. Examples of suitable allylamines antifungal agents include an allylamine antifungal agent selected from the group consisting of amorolfine, butenafine, terbinafine and naftifine and mixtures thereof. These are non-limiting examples of allylamine antifungal agents. Terbinafine is the most preferred allylamine antifungal agent according to the invention.

The amount of allylamine in the formulation is from 1% to 12%, Preferably the amount of allylamine is about 10%. 12% is the approximate limit of solubility of an allylamine in the inventive formulation, Preferably the amount of allylamine is from 5% to 12%, more preferably from 8% to 12%, and most preferably from 10.5% to 12%. However, the solubility of an allylamine may vary depending on the temperature and the quality of the included compounds. Alternatively, when the upper limit of solubility of allylamine in the composition is 11.5% the preferred amount of allylamine is from 5% to 11.5%, more preferably from 8% to 11.5%, and most preferably from 10.5% to 11.5%.

The invented composition contains an organic acid or an ester thereof and an alcohol. This results in a surprisingly high solubility and delivery into and through keratinized tissue of an allylamine antifungal compound.

The organic acid is a C1-8 carboxylic acid. Examples of C1-8 carboxylic acid include any one or more of saturated or unsaturated, straight or branched aliphatic mono-, di- and polycarboxylic acids having 1, 2, 3, 4, 5, 6, 7 or 8 carbon atoms, araliphatic or aromatic dicarboxylic acids, oxy and hydroxyl carboxylic acids (e.g. alpha-hydroxy acids) having 1, 2, 3, 4, 5, 6, 7 or 8 carbon atoms. Examples of suitable organic acid components include one or more of formic acid, acetic acid, propionic acid, butyric acid, valeric acid, caproic acid, sorbic acid, oxalic acid, citric acid, malonic acid, fumaric acid, succinic acid, glutaric acid, apidic acid, pimelic acid, oxalacetic acid, malic acid, tartaric acid, tartronic acid, hydrobutyric acid, hydroxypropionic acid and pyruvic acid. A preferred organic acid is lactic acid.

As an alternative to the organic acid, the composition can include a C1-4 alkyl ester of a suitable organic acid, or a mixture of a suitable organic acid and an ester of the organic acid. A preferred ester is an ester of lactic acid. Non-limiting examples of suitable esters are methyl lactate, ethyl lactate, butyl lactate and propyl lactate.

The organic acid or ester thereof or mixture thereof is present in the composition in amounts of from 1% to 30%, more preferably from 5% to 25%, even more preferably from 7% to 22% and most preferably from 8% to 20%.

Suitable dials are propanediol, butanediol, pentanediol, and hexanediol, were propanediol and butanediol are particularly suitable. Mixtures of the mentioned dials are also suitable.

The dials, or mixtures of them, shall preferably be used in a amount of more than 50%, more preferably from 50% to 95%, even more preferably from 50% to 90%, even more preferably from 60% to 90% and most preferably about from 67.5% to about 84%.

The composition comprises a sequestration agent. The addition of a sequestration agent surprisingly increases the delivery of allylamine into the nail. Non-limiting examples of suitable sequestration agents include one or more of aminoacetic acids, phosphonates, phosphonic acids and mixtures of these. Sequestration agents con be metal complexing agents that may form a complex with metals such as the alkali metals or alkaline. earth metals. A preferred sequestration agent is ethylenediaminetetraacetic acid (EDTA). Examples of suitable amounts of the sequestration agent include from 0.01% to 5%, preferably from 0.02% to 3%, more preferably from 0.03% to 1%.

The composition preferably comprises from about 67.5% to about 84% of propanediol, from 8% to 20% of lactic acid, from 0.03% to 0.1% of EDTA and from 8% to 12% of terbinafine.

Preferred compositions according to the invention are also those of examples A, B, C, D, E, F, G, H, I, J, K, ISM09024, ISM09017, ISM09018, and ISM09016 in the examples section.

The formulation can comprise other components that will be beneficial to the effect and stability of the formulation. Examples of such ingredients are urea, sulfhydryl group-containing amino acids and other keratin degrading agents. Examples of keratin degrading agents are cysteine, acetyl cysteine and mercapto acids.

Components that improve the texture of the formulation such as polymers and other viscosity enhancers, as well as masking and coloring agents may be added as well. Furthermore, standard dermatological components with buffering capacity and anti microbial properties can be added to the formulation provided that the ingredients are soluble in and compatible with the novel composition.

The inventive formulation is intended to be applied to a nail. The formulation is intended for use to treat fungal infections of a nail. However, the inventive formulation can also be used to treat fungal infections of other types of keratinized tissue, such as a callous.

In a second main aspect of the invention there is provided the use of the inventive composition for the treatment of fungal infection of the nail.

In a third main aspect of the invention there is provided a method for treatment of fungal infection of the nail wherein a composition according to the invention is administered to the nail of a patient.

EXAMPLES

In order to evaluate the effect of the invented formulations we have used an in vitro penetration method, the Franz cell. We have used hoof membranes as substitute for nails. The hoof is an acceptable model for human nails in this type of experiment (Mertin, D. Lippold, B. C. "In-vitro permeability of the human nail and of a keratin membrane from bovine hooves: prediction of the penetration rate of antimycotics through the nail plate and their efficacy" J Pharm Pharmacol, 1997, 49 (9) 866-72)(cit. Mertin and Lippold 1997).

The in vitro drug penetration experiments are carried out as described in Mertin and Lippold, 1997. The experiments were carried out as follows. 0.1 M citrate buffer, pH 3.7 was used as receptor solution in the Franz cell. The receptor solution was degassed 10 min with helium before the experiment. Only hoof membranes from the sole of the bovine hoof were used. Terbinafine was used in the form of terbinafine hydrochloride.

The hoof membranes were mounted in the diffusion cells after 15 minutes of hydration. Sampling was done after allowing diffusion for six hours. All in vitro penetration experiments have been performed in triplicates.

The flux was normalized to the flux of a 1% terbinafine, Therefore, the flux is here described as µg of terbinafine/% tbf*h*cm$^2$ and the results from the penetration experiments has been calculated according to the equation:

$$\text{Normalized flux} = \Delta m/(\Delta t * A * \% \ tbf)$$

Where
$\Delta m$=mass increase of terbinafine in the receptor fluid in µg
$\Delta t$=time between observations in hours
A=membrane surface area in cm$^2$
% tbf=the weight percentage of terbinafine in the composition.

Example 1

Terbinafine Flux at Different Levels of Lactic Acid in the Formulation

The effect of lactic acid in the formulation is demonstrated in this experiment. The increase of lactic acid from 0% to 20% generated a flux that was two times higher (composition C compared to composition E in Table 1).

TABLE 1

| Composition | C | D | E |
|---|---|---|---|
| Ingredients/Lab prot | | | |
| Propanediol | 90 g | 80 g | 70 g |
| Lactic acid | — | 10 g | 20 g |
| Terbinafine | 10 g | 10 g | 10 g |

TABLE 1-continued

| Composition | C | D | E |
|---|---|---|---|
| Penetration data | | | |
| Flux µg/cm2 * hour | 37.97 | 58.88 | 74.5 |
| Relative Standard Deviation | 26.2 | 12.5 | 1.38 |
| Normalized flux | 0.65 | 1 | 1.27 |

Example 2

In this example propanediol has been partly replaced with other diols. Pentanediol seems to have the same effect on the penetration as propanediol which performs better than hexanediol from a penetration point of view.

TABLE 2

| Composition | F | G | H |
|---|---|---|---|
| Ingredients/Lab prot | | | |
| Propanediol | 69 g | 35 g | 28 g |
| Lactic acid | 10 g | 10 g | 10 g |
| Urea | 10 g | 10 g | 10 g |
| Pentane diol | — | — | 42 g |
| Hexanediol | — | 35 g | — |
| Terbinafine | 10 g | 10 g | 10 g |
| Penetration data | | | |
| Normalised flux | 1 | 0.92 | 1 |

Example 3

The relationship between the amount of urea and terbinafine penetration was investigated. Introduction of urea in the formulation had no effect on the penetration of terbinafine.

TABLE 3

| Composition | I | J | K | L |
|---|---|---|---|---|
| Ingredients/Lab prot | | | | |
| Urea | 0 | 2 g | 5 g | 10 g |
| Propanediol | 80 g | 78 g | 75 g | 70 g |
| Lactic acid | 10 g | 10 g | 10 g | 10 g |
| Terbinafine | 10 g | 10 g | 10 g | 10 g |
| Penetration data | | | | |
| Normalised flux | 1 | 0.9 | 1 | 1 |

Example 4

Compositions Containing Combination of Urea and Acetylcysteine

TABLE 4

| Composition | ISM09024 | ISM09017 | ISM09018 | ISM09016 |
|---|---|---|---|---|
| Ingredients/Lab prot | | | | |
| Urea | 10 g | 10 g | 10 g | 15 g |
| Propanediol | 70 g | 60 g | 50 g | 50 g |
| Lactic acid | 10 g | 10 g | 10 g | 10 g |
| Acetylcysteine | — | 10 | 20 | 15 |

TABLE 4-continued

| Composition | ISM09024 | ISM09017 | ISM09018 | ISM09016 |
|---|---|---|---|---|
| Terbinafine | 10 g | 10 g | 10 g | 10 g |
| Penetration data | | | | |
| Normalised flux | 1 | 1.41 | 1.39 | 1.84 |

In this experiment four compositions were manufactured. The compositions are listed in table 4 and manufacturing was performed by dissolution of the ingredients in propanediol.

In table 4 there is a 40% increase in flux when acetyl cysteine is incorporated in the formulation. Increase of concentration of acetyl cysteine does not increase the flux. However, keeping the ratio of urea to acetyl cysteine at 1:1 and increasing the concentration of both to from 10% to 15% leads to an increase in flux of 40%.

Example 5

Effect of EDTA

In attempts to stabilize the components of the invented composition EDTA was added to the formulation. In the in vitro experiments we surprisingly found that the flux of terbinafine increased by 30% from an already high level. Data is presented in Table 5.

TABLE 5

| Composition | A | B |
|---|---|---|
| Ingredients/Lab prot | | |
| Propanediol | 80 g | 79.95 g |
| Lactic acid | 10 g | 10 g |
| EDTA | — | 0.05 g |
| Terbinafine | 10 g | 10 g |
| Penetration data | | |
| Flux µg/cm2 * hour | 45.0 | 58.18 |
| Relative Standard Deviation | 4.89 | 6.29 |
| Normalised flux | 1.84 | 2.37 |

The invention claimed is:

1. A pharmaceutical composition for the treatment of onychomycosis of the nail comprising terbinafine present in solution in an amount of more than 5%, in a mixture of an organic acid or an ester thereof present in an amount of 1% to 30%, a diol present in an amount of about 50% to 95%, and EDTA present in an amount of from 0.01% to 5%, which composition comprises sufficiently low amounts of water to prevent precipitation said terbinafine from said solution wherein:
   said diol is selected from the group consisting of propanediol, butanediol, pentanediol and hexanediol;
   said organic acid is selected from the group consisting of saturated or unsaturated, straight or branched aliphatic mono-, di- or polycarboxylic acids having 1-8 carbon atoms, araliphatic dicarboxylic acids having 1-8 carbon atoms, aromatic dicarboxylic acids having 1-8 carbon atoms, oxy-carboxylic acids having 1-8 carbon atoms, and hydroxyl-carboxylic acids having 1-8 carbon atoms; and
   said ester of the organic acid is one or more C1-4 alkyl esters of said organic acid.

2. The composition according to claim 1, wherein the organic acid is selected from the group consisting of formic acid, acetic acid, propionic acid, butyric acid, valeric acid, caproic acid, sorbic acid, oxalic acid, citric acid, malonic acid, fumaric acid, succinic acid, glutaric acid, apidic acid, pimelic acid, oxalacetic acid, malic acid, tartaric acid, tartronic acid, hydrobutyric acid, hydroxypropionic acid, pyruvic acid and lactic acid.

3. The composition according to claim 2, wherein the organic acid is lactic acid.

4. The composition according to claim 1, wherein the organic acid or ester thereof is present in an amount of 5% to 25%.

5. The composition according to claim 1, wherein the terbinafine is present in an amount of from 5% to 12%.

6. The composition according claim 5, wherein the terbinafine is present in a amount of from 8% to 11.5%.

7. The composition according to claim 1, comprising from about 67.5% to about 84% of propanediol, from 8% to 20% of lactic acid, from 0.03% to 0.1% EDTA and from 8% to 12% of terbinafine.

8. The composition according to claim 3, comprising from about 67.5% to about 84% of propanediol, from 8% to 20% of lactic acid, from 0.03% to 0.1% EDTA and from 8% to 12% of terbinafine.

9. A method of treatment of onychomycosis of the nail, wherein a composition according to claim 1 is administered to the nail of a patient.

10. The pharmaceutical composition according to claim 1, wherein said pharmaceutical composition increases delivery of the terbinafine into the nail as compared to said pharmaceutical composition not comprising EDTA.

* * * * *